(12) United States Patent
Pourdeyhimi et al.

(10) Patent No.: US 8,535,727 B2
(45) Date of Patent: Sep. 17, 2013

(54) BIODEGRADABLE NON-WOVEN FABRIC HAVING PLANT VIRUS ENCAPSULATED ACTIVES FOR DRUG DELIVERY

(75) Inventors: Behnam Pourdeyhimi, Cary, NC (US); Steve A. Lommel, Cary, NC (US); Sara Honarbakhsh, Cincinnati, OH (US); Ruben Carbonell, Raleigh, NC (US); Richard H. Guenther, Cary, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 13/203,017

(22) PCT Filed: Feb. 25, 2010

(86) PCT No.: PCT/US2010/025374
§ 371 (c)(1),
(2), (4) Date: Sep. 29, 2011

(87) PCT Pub. No.: WO2010/099292
PCT Pub. Date: Sep. 2, 2010

(65) Prior Publication Data
US 2012/0015020 A1    Jan. 19, 2012

Related U.S. Application Data

(60) Provisional application No. 61/155,407, filed on Feb. 25, 2009.

(51) Int. Cl.
*A61K 9/50* (2006.01)
(52) U.S. Cl.
USPC ........... 424/501; 977/773; 977/802; 977/805; 977/906

(58) Field of Classification Search
None
See application file for complete search history.

(56) References Cited

U.S. PATENT DOCUMENTS

| 6,048,551 | A | 4/2000 | Hilfinger et al. |
|---|---|---|---|
| 2006/0263417 | A1 | 11/2006 | Lelkes et al. |
| 2008/0063604 | A1 | 3/2008 | Claudio |
| 2008/0220054 | A1 | 9/2008 | Shastri et al. |

OTHER PUBLICATIONS http://repository.lib.ncsu.edu/ir/handle/1840.16/4143, Franzen, Jan. 2009.*
Franzen et al, "Targeting Cancer with Smart Bombs: Equipping Plant Virus Nanoparticles for a 'Seek and Destroy' Mission", Nanomedicine (2009), 4(5) 55-588.*
Xie, J., et al., "Putting Electrospun Nanofibers to Work for Biomedical Research," *Macromolecular Rapid Communications*, 29(22): 1775-1792 (2008).
Lu, P., et al., "Applications of Electrospun Fibers," *Recent Patents on Nanotechnology*, 2: 169-182 (2008).
Loo, LiNa, et al., "Infusion of Dye Molecules Into Red Clover Necrotic Mosaic Virus," *Chem. Commun.*, 88-90 (2008).
Nicolae, Cristian-Andi, "An Investigation of Thermal Degradation of Poly (Lactic Acid)," *Advanced Online Publication* (2008).

(Continued)

*Primary Examiner* — Carlos Azpuru
(74) *Attorney, Agent, or Firm* — Womble Carlyle Sandridge & Rice, LLP

(57) ABSTRACT

A biodegradable delivery system for actives such as pharmaceutical drugs. The delivery system includes actives infused into the capsid of a purified plant virus. The loaded capsids are embedding in electrospun biodegradable polymer fibers, forming a nonwoven fabric.

8 Claims, 3 Drawing Sheets

(56) References Cited

OTHER PUBLICATIONS

Hegde, Raghavendra, et al, "Nanfiber Nonwovens," http://www.engr.utk.edu/mse/Textiles/Nanofiber%20Nonwovens.htm (2009).

Buschle-Diller, Gisela, et al. "Electrospun Nanofibers From Biopolymers and Their Biomedical Applications," *Springer Netherlands*, Chapter 5 (2006).

Kwangsok, Kim, et al. "Incorporation and Controlled Release of a Hydrophilic Antibiotic Using Poly (Lactide-Co-Glycolid)—Based Electrospun Nanofibrous Scaffolds," *Science Direct—Journal of Controlled Release*, vol. 98, Issue 1 (2004) http://www.sciencedirect.com/science/article/pii/S0168365904001932 (2004).

* cited by examiner

BIODEGRADABLE NON-WOVEN FABRIC HAVING PLANT VIRUS ENCAPSULATED ACTIVES FOR DRUG DELIVERY

CROSS-REFERENCE TO RELATED APPLICATIONS

This application is a national phase of International Application PCT/US10/025374, filed Feb. 25, 2010, which claims priority under 35 USC §119 to U.S. Provisional Application No. 61/155,407, filed Feb. 25, 2009, each of which is herein incorporated by reference in its entirety.

FIELD OF THE INVENTION

The present invention pertains to drug or "active" delivery systems formed of biodegradable and biocompatible nanofibrous polymeric fabrics having nanoparticles of a certain plant virus preloaded with an active such as a pharmaceutical, therapeutic, or diagnostic compound or reagent.

BACKGROUND

Smart materials that monitor and respond to changing conditions have a wide range of practical applications. For example, pharmaceuticals or drugs encapsulated within biodegradable polymers may be used to yield controlled release functionality. In other examples, drugs encapsulated within soluble polymers achieve similar results, i.e. being responsive to the surrounding environment. However, these methods have not found wide application with engineered fibrous structures, such as nonwovens and other textiles, in part because of polymer-to-process compatibility limitations. Thus, smart fabrics engineered from fibrous materials have been elusive.

Nonwoven fabrics are typically formed directly from fibers (i.e. staple fibers) or polymers. Fabric formation directly from polymers is referred to as direct spinning and includes either melt spinning a thermoplastic polymer or solution spinning Direct spinning, however, typically yields larger fiber diameters, e.g. 30 to 40 microns and higher. In addition, a limited number of polymers, and blends of polymers, are compatible with direct spinning methods. While the direct spinning methods are amenable to varied fiber diameter or shapes, complex equipment configurations and additional processing are required.

SUMMARY

An active delivery system made up of a biodegradable and biocompatible nonwoven fabric formed from electrospun fibers of at least one biodegradable and biocompatible polymer. The fibers have nanoparticles of a plant virus imbedded in, or carried on the surface of the fiber. The nanoparticles are capable of holding and releasing an active.

DETAILED DESCRIPTION OF THE INVENTION

Certain exemplary embodiments of the present invention are described below and illustrated in the accompanying figures. The embodiments described are only for purposes of illustrating the present invention and should not be interpreted as limiting the scope of the invention, which, of course, is limited only by the claims below. Other embodiments of the invention, and certain modifications and improvements of the described embodiments, will occur to those skilled in the art, and all such alternate embodiments, modifications, and improvements are within the scope of the present invention.

A biodegradable and biocompatible nonwoven nanofabric has been developed that comprises fiber and/or nanofibers having plant virus nanoparticles (PVN) imbedded therein or on the surface thereof, the PVN being preloaded with one or more actives. The actives are carried within the PVN and may provide pharmaceutical, therapeutic, or diagnostic benefits to the relevant in vivo locations, i.e. the delivery site, with minimal adverse effects. The delivery site refers to the location where the nanofiber nonwoven fabric is placed. The delivery site includes, but is not limited to, a human or mammalian tissue or tumor, or any implant for insertion in a human or mammalian body. As the nanofiber fabric biodegrades, the plant virus nanoparticles are exposed and the actives are released. The rate of biodegrading may, in part determine the release of the actives. In some embodiments, because the virus nanoparticles are on or near the surface of the fabric, exposure of the virus and the release of the actives initiates when the nanofiber fabric initially contacts the delivery site. In other embodiments, exposure and release may be delayed.

Figure 1A:
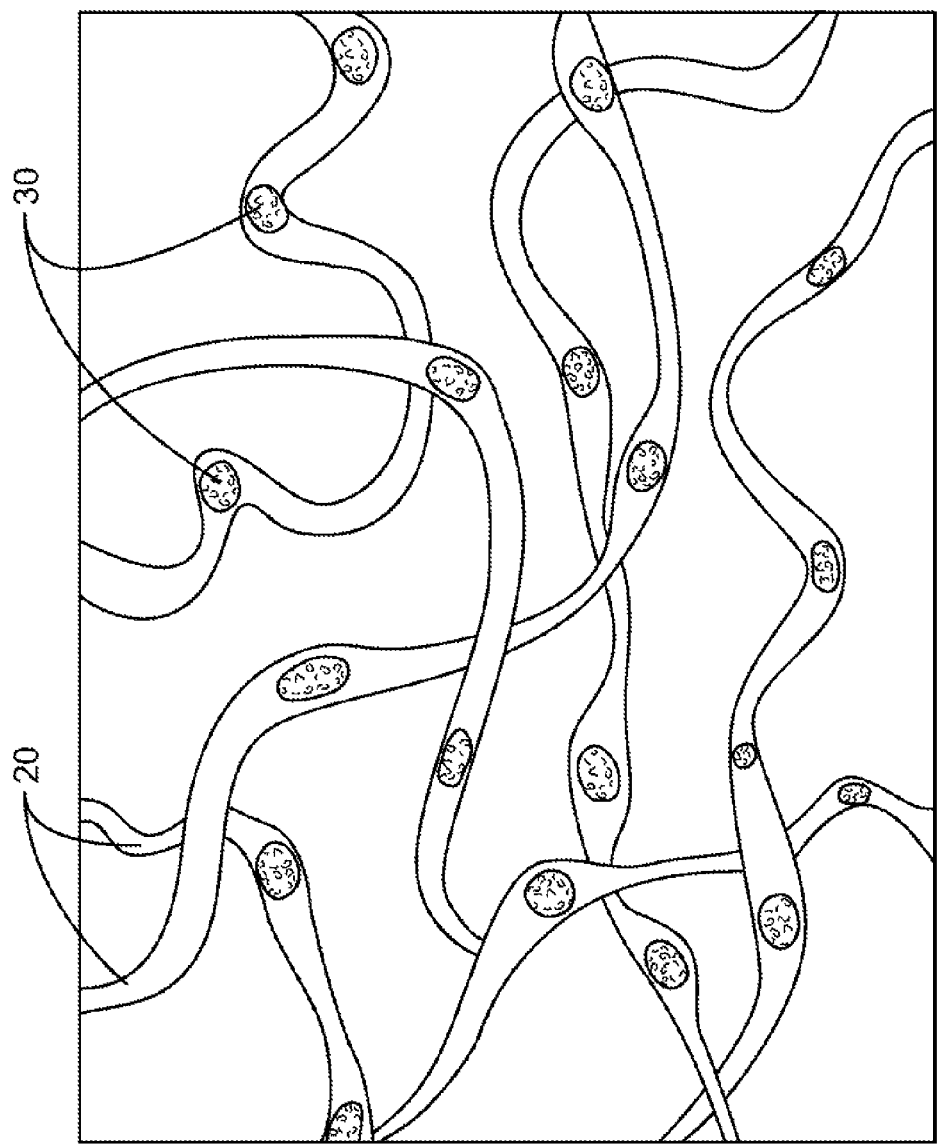
FIGS. 1A and 1B show representations of embodiments of a nanofiber nonwoven fabric with nanoparticles of a plant virus.
Figure 1B:
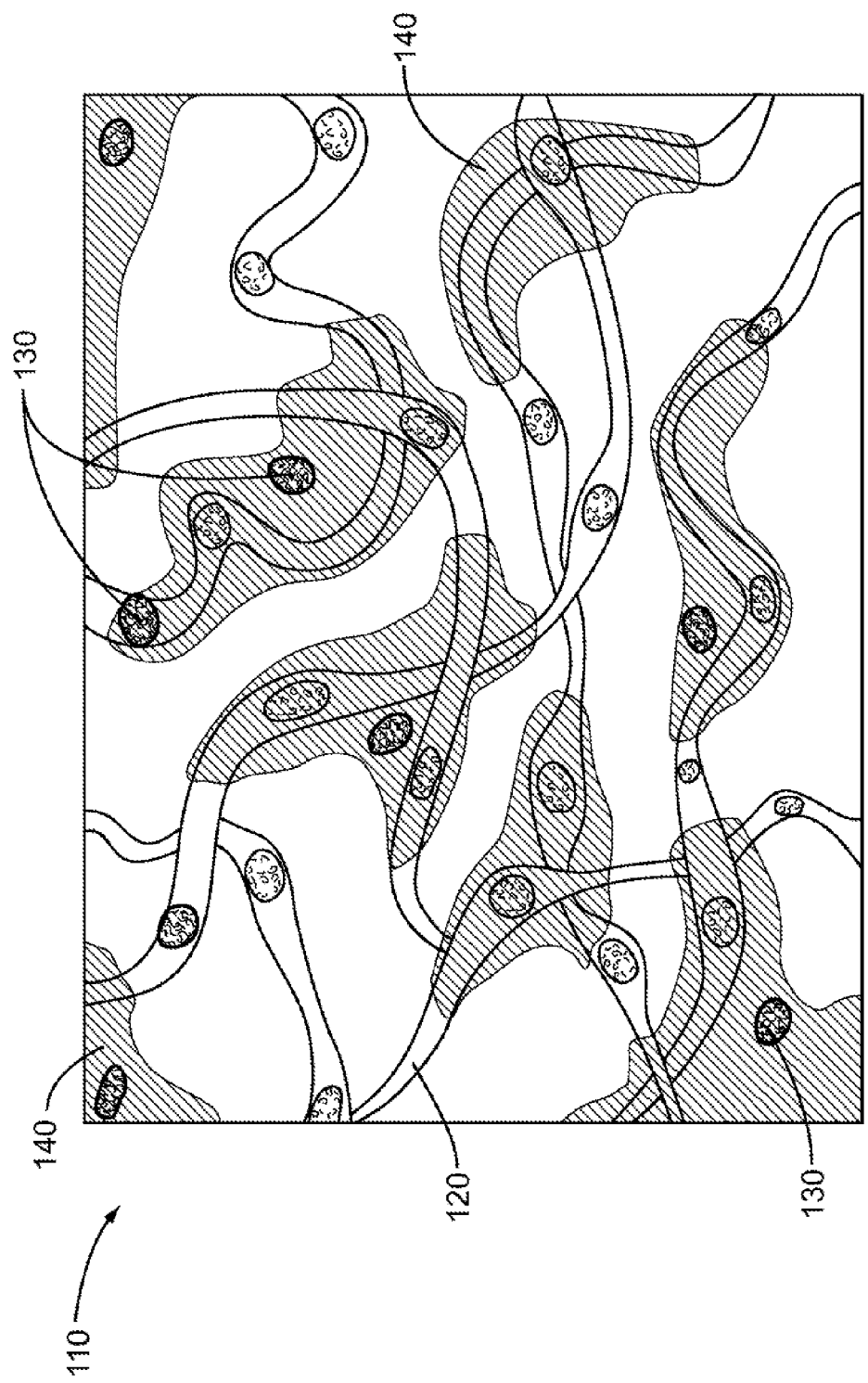

As shown in FIGS. 1A and 1B, the nonwoven fabric 10 includes nanofibers 20 formed from biodegradable and biocompatible polymers and having PVNs 30 imbedded therein or carried on the surface thereof. The PVN's are loaded with one or more actives, i.e., the polymer may be co-spun with the loaded PVN. "Nanofibers," as used herein, refers to fibers with an outer diameter from about 20 nm up to about 50 µm, and include some microfibers with an outer diameter up to about 50 µm. As used herein, the phrase "loaded PVN" refers to a plant virus nanoparticle with one or more actives loaded inside. While the loaded PVN 30 is shown in FIG. 1A as embedded within the nanofiber 20, the loaded PVN may be in or on the surface of the nanofiber 20. In another embodiment, as shown in FIG. 1B, the nanofiber fabric 110 includes a coating of a loaded PVN solution 140 on the nanofiber fabric 110. Accordingly, an embodiment of the invention includes a nanofiber fabric with loaded PVN's 130 inside, coated on the nanofibers, in addition to the loaded PVN's in a coating on the nanofiber fabric. Electrospinning is one suitable method for forming the nanofiber nonwoven fabrics with loaded PVNs shown in FIGS. 1A and 1B.

A wide variety of virus nanoparticles may be used as long as they are harmless to the human or other mammalian subject, can be embedded in or on the nanofiber, and will encapsulate one or more actives. For example, the nanofiber nonwoven fabric can comprise a plurality of viruses of a single family, genus, species or strain; or a plurality of different families, genus, species or strains of viruses. In an embodiment, the plant virus is a member of a family of plant viruses classified as Tombusviridae. In one embodiment, the plant virus belongs to the genus *Dianthovirus*. Other plant viruses include certain viruses belonging to the family Comoviridae or Bromoviridae. For example, the virus can be a Comovirus. In other embodiments, the plant virus is a Sobemovirus. As will be readily appreciated by those skilled in the art, the virus serves as a platform carrier for the active. Thus, as noted, a wide variety of viruses, or combinations thereof, mat be useful in the present invention.

In exemplary alternate embodiments, the nanoparticle is a virus-like particle comprising viral coat protein and viral genome. In other embodiments, the nanoparticle is a virus-like nanoparticle comprising viral coat protein but lacking a viral genome.

In an exemplary embodiment, the exemplary plant virus nanoparticles are plant virus capsids or capsid-like structures, namely, red clover necrotic mosais virus (RCNMV). RCNMV is a single stranded RNA plant virus of the Tombusviridae family and the *dianthovirus* genus. Other types of plant viruses, however, may be suitable for use in a nanofiber fabric as cargo carrying capsids including, artichoke mottled crinkle virus, Carnation Italian ringspot virus, cucumber necrosis virus, cymbidium ringspot virus, Eggplant mottled crinkle virus, Grapevine Algerian latent virus, Lato River virus, Moroccan pepper virus, Neckar River virus, pelargonium leaf curl virus, petunia asteroid mosaic virus, sitke waterborne virus, and the tomato bushy stunt virus.

RCNMV is a robust plant virus that is viable in several environments while being substantially inert to human, or other mammalian tissue. The RCNMV exists within, and outside of, plant and animal cells and has been found in soil, fresh and saltwater environs. RCNMV is combinable with biodegradable and biocompatible polymers as described herein and the structural integrity of RCNMV is maintained throughout electrospinning the nanofiber nonwoven fabric.

RCNMV has a viral structure suitable for receiving and carrying actives within its protein walls. The RCNMV has 180 copies of a capsid protein arranged to form a T=3 icosahedral virion. Each capsid protein packages either 1 copy of a single stranded RNC-1 and RNA-2 or 4 copies of RNA-2. The RCNMV has an outer diameter of about 36.6 nm and an inner cavity with a diameter of about 17 nm. The inner cavity of a RCNMV is capable of receiving any molecule or species with a diameter less than about 20 angstrom. In alternate embodiments, however, other viral structures can be used, such as those with a less dense or hollow core. For example, the virus can be a member of another family of ichosahedral viruses including but not limited to Bromoviridae, Comoviridae, or Tombusviridae. More or less capsid protein copies can form the outershell, depending upon the particular plant virus selected.

In an exemplary embodiment, the PVNs may be selectively opened and closed as needed to either load actives into the capsid shell, or to release actives from the capsid shell. The RCNMV is one such exemplary virus. The RCNMV has divalent ions arranged within and around the 180 capsid protein units. Selective removal of the divalent ions reorients the capsid protein shell and protruding domains and opens a pathway for the infusion of actives into the inner cavity of the virus. The divalent ions include about 360+/−$Ca^{2+}$ ions and about 420+/−$Mg^{2+}$ ions and the selective removal of these ions open and close RCNMV as needed. Thus, the introduction of RCNMV, or other loaded PVN, into calcium or magnesium rich mediums may facilitate opening and closing of the capsid protein shell. In addition to divalent ion removal, modifying the pH of the medium surrounding the RCNMV facilitates the opening and closing of the plant virus capsid. For example, a pH of about 5.0 may open the RCNMV virus and a pH of about 8.0 may close the RCNMV virus.

The loading of the actives within the PVN is repeatable and scalable. Initially, the plant virus nanoparticle is purified in a water and buffer solution. A chelating agent, such as (ethylenediaminetetraacetic acid) EDTA is added to the purified virus to remove the divalent ions causing rotation of the capsid protein copies. The rotation of the capsid proteins opens channels to the inner cavity of the plant virus nanoparticle, as described above. A selected active is then loaded into the plant virus capsid and the active-plant virus solution rests for about one hour. Following the loading step, Calcium ($Ca^{2+}$) and/or Magnesium ($Mg^{2+}$) are added back to the plant virus capsid rotating the capsid protein copies to close the channels, thus encapsulating the active within the inner cavity of the PVN. The load PVN is then suspended in a water-buffer solution for a period of time. In other alternate embodiments, in vitro assemblage may be used to incorporate an active within a plant virus nanoparticle. The loaded PVN, e.g. the loaded RCNMV, may be co-spun with one or more polymers and electrospun into a nanofiber nonwoven fabric.

The RCNMV virus can be loaded with a variety of drugs, actives or other compounds. Non-limiting examples of an active compound or active as used herein include pharmaceuticals, therapeutics, prophylactics, diagnostic or other reagents, and cosmetic agents (e.g., an active toxin of bacterial or plant origin). Further, the active can be, but is not limited to, a chemotherapeutic, a toxin, antineoplastic or cytotoxic compounds, a radiotherapeutic, a radiosensitizing agent, fluorescent compound or chemiluminescent compound, an imaging agent (e.g. fluorescent molecules, such as ethidium bromide (EtBr), dyes, radio-labeled molecules), and combinations thereof. Also, the type of active may vary, for example, it can be characterized as a chemical compound, a small molecule, a ligand, a polypeptide, a nucleic acid (e.g., an antisense nucleic acid construct, a gene therapy vector), or conjugates thereof. In one embodiment, the active is selected from the group consisting of an antibiotic (e.g., ampicillin (AMP), novanthrone (NOVA) or mitoxanthrone), an anthracycline (e.g., doxorubicin (DOX)), an anti-mitotic drug (e.g., taxol, vincristine, vinblastine), an antimetabolite (e.g., methotrexate), an alkylating agent, an immunosuppressant, a hormone, and a radionuclide.

Compounds as used herein also include, but are not limited to, radiolabels (e.g., $^{35}S$, $^{125}I$, $^{32}P$, $^{3}H$, $^{14}C$, $^{131}I$) enzyme labels (e.g., horseradish peroxidase, alkaline phosphatase), gold beads, chemiluminescence labels, ligands (e.g., biotin, digoxin) and/or fluorescence labels (e.g., rhodamine, phycoerythrin, fluorescein), a fluorescent protein including, but not limited to, green fluorescent protein or one of its many modified forms, a nucleic acid segment in accordance with known techniques, and energy absorbing and energy emitting agents.

"Active compound" as used herein includes, but is not limited to, cytotoxic nucleosides or nucleotides, antisense oligonucleotides, radionuclides, energy absorbing and energy emitting agents, and other cytotoxic agents. Other cytotoxic (or "antineoplastic") agents include, but are not limited to, ricin (or more particularly the ricin A chain), aclacinomycin, diphtheria toxin, Monensin, Verrucarin A, Abrin, Tricothecenes, and Pseudomonas exotoxin A, taxol, cytochalasin B, gramicidin D, ethidium bromide, emetine, mitomycin, etoposide, tenoposide, anti-mitotic agents such as the vinca alkaloids (e.g., vincristine and vinblastine), colchicin, anthracyclines (e.g., doxorubicin, daunorubicin, epirubicin and idarubicin and analogs thereof), dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof, antimetabolites (e.g., methotrexate, 6-mercaptopurine, 6-thioguanine, cytarabine, and 5-fluorouracil decarbazine), alkylating agents (e.g., mechlorethamine, thiotepa, chlorambucil, melphalan, carmustine (BSNU), lomustine (CCNU), cyclothosphamide, busulfan, dibromomannitol, streptozotocin, mitomycin C, and cis-dichlorodiamine platinum (II) (DDP)), and antibiotics, including but not limited to, dactinomycin (formerly actinomycin), bleomycin, mithramycin, calicheamicin, and anthramycin (AMC).

Additional examples of antineoplastic or cytotoxic compounds that may be used as active compounds herein include but are not limited to: cisplatin, doxorubicin, taxotere, taxol, etoposide, irinotecan, camptostar, topotecan, paclitaxel, docetaxel, epothilones, tamoxifen, 5-fluorouracil, methoxtrexate, SFU, temozolomide, cyclophosphamide, SCH 66336, R115777, L778,123, BMS 214662, Iressa, Tarceva, antibodies to EGFR, Gleevec, intron, ara-C, adriamycin, cytoxan, gemcitabine, Uracil mustard, Chlormethine, Ifosfamide, Melphalan, Chlorambucil, Pipobroman, Triethylenemelamine, Triethylenethiophosphoramine, Busulfan, Carmustine, Lomustine, Streptozocin, Dacarbazine, Floxuridine, Cytarabine, 6-Mercaptopurine, 6-Thioguanine, Fludarabine phosphate, oxaliplatin, leucovirin, ELOXATIN™, Pentostatine, Vinblastine, Vincristine, Vindesine, Bleomycin, Dactinomycin, Daunorubicin, Doxorubicin, Epirubicin, Idarubicin, Mithramycin, Deoxycoformycin, Mitomycin-C, L-Asparaginase, Teniposide 17.alpha-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, goserelin, Carboplatin, Hydroxyurea, Amsacrine, Procarbazine, Mitotane, Mitoxantrone, Levamisole, Navelbene, CPT-11, Anastrazole, Letrazole, Capecitabine, Reloxafine, Droloxafine, or Hexamethylmelamine; a mechlorethamine, chlorambucil, cyclophosphamide, melphalan, ifosfamide, methotrexate, 6-mercaptopurine, 5-fluorouracil, cytarabile, gemcitabine, vinblastine, vincristine, vinorelbine, paclitaxel, etoposide, irinotecan, topotecan, doxorubicin, bleomycin, mitomycin, carmustine, lomustine, cisplatin, carboplatin, tamoxifen, leuprolide, flutamide, and megestrol, imatinib, adriamycin, dexamethasone, or cyclophosphamide Active compounds may be oligonucleotides, e.g., DNA, RNA, cDNA, PNA, genomic DNA, and synthetic oligonucleotides, such as antisense ologicnueltides, etc. Such olgionucleotides are typically from 10, 12 or 15 nucleotide bases in length up to 30, 50 or 100 nucleotide bases in length, or more. Active compounds may be noncoding regulatory RNAs.

"Noncoding regulatory RNAs" (ncRNA) as used herein includes both natural and synthetic ncRNAs. Examples include, but are not limited to, small interfering RNA (siRNA), micro RNA (miRNA), piRNAs, ribosomal RNA (rRNA), small nuclear RNA (snRNA), small non-mRNA (sn-mRNA), small nucleolar RNA (snoRNA), small temporal RNA (stRNA) and other RNAs that regulate the function of mRNAs. Some ncRNAs may be in the form of a natural or synthetic short hairpin RNA or "shRNA," which short hairpin RNA may or may not be subsequently processed to form a mature ncRNA. In general, ncRNAs as used herein may be any suitable length, but are typically short, e.g., from 5, 10 or 15 nucleotides in length, up to 25, 30 or 35 nucleotides in length. Nucleic acids encoding ncRNAs as used herein may be natural or synthetic and may be derived from any suitable source, including plant, animal, and microbe sources as described herein.

"Small interfering RNA" or "siRNA" (sometimes also referred to as short interfering RNA or silencing RNA) as used herein has its ordinary meaning in the art. In general, siRNAs are double-stranded RNA molecules that are 15 or 20 nucleotides in length, up to 25 or 30 nucleotides in length. siRNAs are known.

"MicroRNA" or "miRNA" as used herein has its ordinary meaning in the art. Typically, a miRNA is an RNA molecule derived from genomic loci processed from transcripts that can form local RNA precursor miRNA structures. The mature miRNA usually has 20, 21, 22, 23, or 24 nucleotides, although in some cases it may include a greater of lesser number of nucleotides, for example, between 18 and 26 nucleotides. The miRNA has the potential to pair with flanking genomic sequences, placing the mature miRNA within an imperfect RNA duplex which may be needed for its processing from a longer precursor transcript. In animals, this processing may occur through the action of Drosha and Dicer endonucleases, which excise a miRNA duplex from the hairpin portion of the longer primary transcript. The miRNA duplex comprises the miRNA and a similar-sized segment known as the miRNA* (miRNA star) from the other arm of the stem-loop.

"Radionuclide" as used herein may be any radionuclide suitable for delivering a therapeutic dosage of radiation to a target cell such as a tumor or cancer cell, including but not limited to $^{227}$Ac, $^{211}$At, $^{131}$Ba, $^{77}$Br, $^{109}$Cd, $^{51}$Cr, $^{67}$Cu, $^{165}$Dy, $^{155}$Eu, $^{153}$Gd, $^{198}$Au, $^{166}$Ho, $^{113m}$In, $^{115m}$In, $^{123}$I, $^{125}$I, $^{131}$I, $^{189}$Ir, $^{191}$Ir, $^{192}$Ir, $^{194}$Ir, $^{52}$Fe, $^{55}$Fe, $^{59}$Fe, $^{177}$Lu, $^{109}$Pd, $^{32}$P, $^{226}$Ra, $^{186}$Re, $^{188}$Re, $^{153}$Sm, $^{46}$Sc, $^{47}$Sc, $^{72}$Se, $^{75}$Se, $^{105}$Ag, $^{89}$Sr, $^{35}$S, $^{177}$Ta, $^{117m}$Sn, $^{121}$Sn, $^{166}$Yb, $^{169}$Yb, $^{90}$Y, $^{212}$Bi, $^{119}$Sb, $^{197}$Hg, $^{97}$Ru, $^{100}$Pd, $^{101}$mRh, and $^{212}$Pb.

Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol.

Compounds may include chemically linked fluorescent or chemiluminescent labels to nucleotides is well-known in the art. Exemplary chemiluminescent labels are 1,2-dioxetane compounds. Fluorescent dyes useful for labeling nucleotide 5'-triphosphates include fluoresceins rhodamines, cyanines, and metal porphyrin complexes.

Fluorescein dyes are well-known in the art and include, but are not limited to, fluorescein isothiocyanate, 6-carboxyfluorescein (6-FAM); 2',4',1,4,-tetrachlorofluorescein (TET); 2',4',5',7',1,4-hexachlorofluorescein (HEX); 2',7'-dimethoxy-4',5'-dichloro-6-carboxyrhodamine (JOE); 2'-chloro-5'-fluoro-7',8'-fused phenyl-1,4-dichloro-6-carboxyfluoresccin (NED); and 2'-chloro-7'-phenyl-1,4-dichloro-6-carboxyfluorescein (VIC), CY3™, CYS™, CY3.5™, CY5.5™ and the like.

Electrospinning is used to form the biodegradable and biocompatible polymers and loaded PVNs into a nanofiber nonwoven fabric. A composition comprising a biodegradable polymer-solvent blend and PVN solution is electrospun to form the nanofiber nonwoven fabric comprising the PVN loaded. Electrospinning forms fibers directly from a polymer solution with minimal or very low thermal input during processing. Plant virus capsids that may be heat sensitive, e.g., such as the red clover necrotic mosaic virus (RCNMV), maintain their structural integrity throughout the electrospinning process. In another embodiment, the nanofiber fabric 10 is formed by an electrospinning process such as Nanospider™. The Nanospider™ machine is similar to the electrospinning apparatus described above, however, the polymer solution is poured into a tray in which a rotating electrode is sitting. Rotation of the charged electrode induces charge in the solution and forms nanofibers when the charge overcomes the surface tension of the solution. In other alternate embodiments, other solution spinning methods may be used to form a nanofabric.

Figure 2:
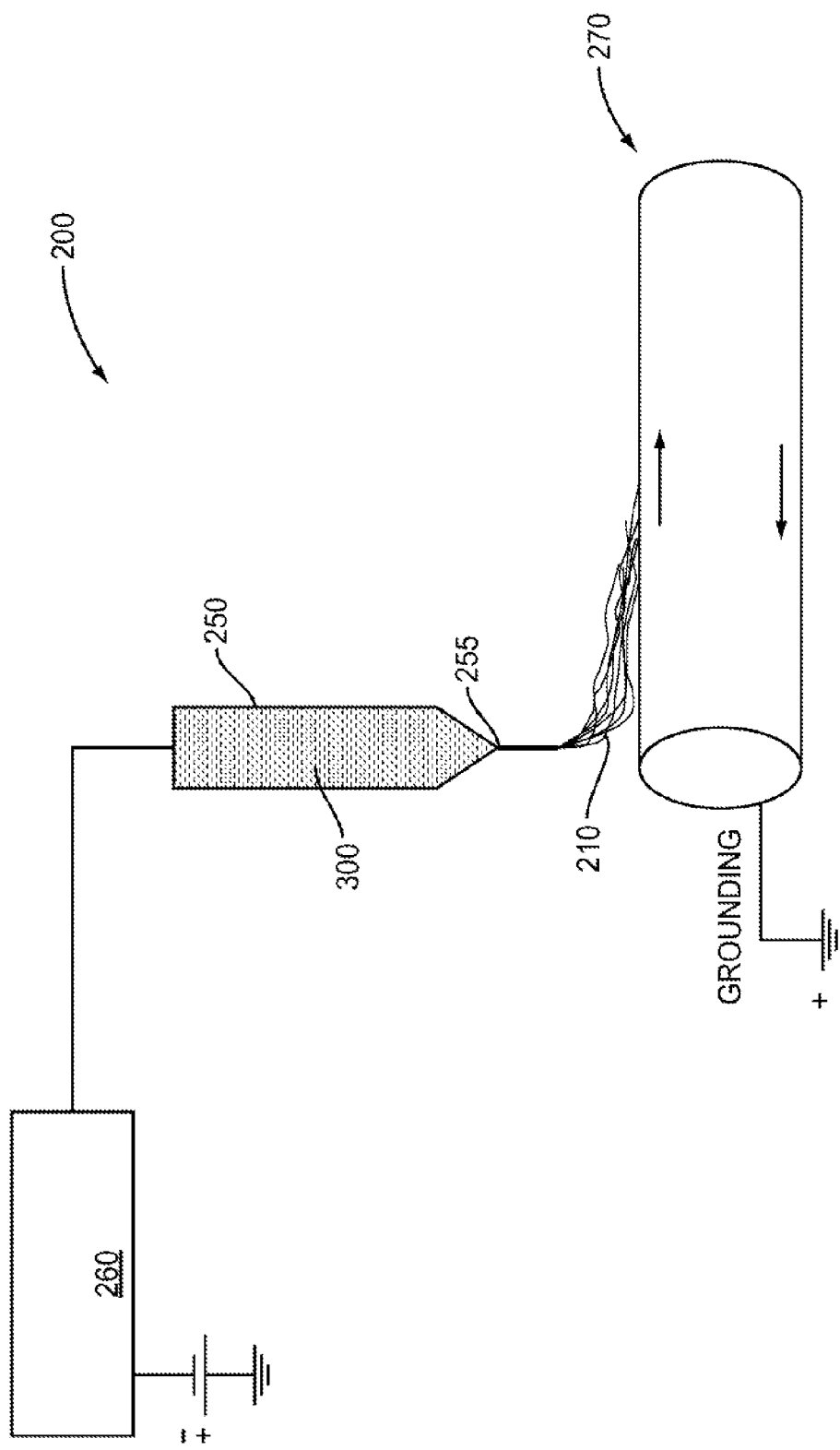
FIG. 2 shows a schematic of an electrospinning process used to form a nanofiber nonwoven fabric.

As shown in FIG. 2, the electrospinning system 200 includes a syringe pump unit 250, a power supply 260 and a grounded collector 270. Electrospinning forms fibers by accelerating a jet of electrically charged polymer solution 300 in an electric field toward a grounded collector 270, such as a collection surface or plate. The syringe pump 250 has a fine capillary 255, such as a needle, positioned at a predetermined distance from a grounded collector 270. A high voltage electric charge introduced to the polymer solution forces fibers 210 through the needle toward the grounded collector 270. The collector 270 grounds the charge while accumulating the co-spun fibers and loaded PVNs into a nonwoven fabric. In other embodiments, the collector 270 may include a textile structure, such as woven, knit or nonwoven upon which the fibers are collected to form a laminate. In still other embodiments, the collector 270 may include a polymeric film upon which the fibers are collected.

In an exemplary embodiment, the polymer solution may be electrospun into a nanofiber nonwoven fabric using between about 8 to 12 EV (e.g. 8 Kv, 10 Kv and 12 Kv were used to form various samples with satisfactory results). The polymer solution flow rate may range between about 0.5-3.0 mL/mn.

As described above, electrospinning forms the nanofiber fabric directly from a polymer solution 300. The polymer solution 300 includes a polymer-solvent blend and a loaded PVN solution. The loaded PVN solution includes the plant virus nanoparticles with the active, and other additives, e.g. a buffer. In an exemplary embodiment, the ratio of the PVN solution to the polymer-solvent blend is about 2:1. In another embodiment, the ratio of PVN solution to the polymers solvent blend is about 2:1. In other embodiments, the ratio may range from about 1:1 to 10:1 of a PVN to polymer-solvent blend. In still other embodiments, the ratio may range from about 1:1 to about 1:10 of PVN to polymer-solvent blend.

The polymer-solvent blend includes one or more polymers in a polymer blend and a solvent. In an exemplary embodiment, the polymer-solvent blend may comprise between about 5 to about 20% by weight of one or more polymers, and between about 80 to 95% by weight of a solvent. In an exemplary embodiment, the polymer concentration is about 12% and solvent concentration is about 88%.

Biodegradable and biocompatible polymers are used to form the nanofiber fabric 10. In an embodiment, hydrophilic polymers are suitable. Exemplary polymers include, but are not limited to, polyglycolic acid, polylactic acid, polyethylene oxide, polycaprolactone (PCL), polyethylenimine-polyethylene glycol, cyclodextrin, and ethylene vinyl acetate poly (L-lysine)-poly(ethylene glycol) (PLL-PEG), polyethylenimine (PEI), poly(a-[4-aminobutyl]-1-glycolic acid) (PAGA), cyclodextrin (CD), Poly(2-(dimethylamino) ethyl methacrylate) (pDMAEMA), poly(vinyl alcohol) (PVA), poly(enol-ketone) (PEK) and N-(2-hydroxypropyl) methacrylamide (HPMA) copolymers, copolymers of each, and any combination thereof. The polymers listed above may be used alone or combined with one or more of the others. For example, in an embodiment, a first polymer and second polymer may be combined in a polymer blend in any particular weight percent. For example the first polymer may comprise between about 1% to about 99% of the total polymers in the polymer-solvent blend, while a second polymer comprises the balance of the total polymer in the polymer-solvent blend. For example, the second polymer may comprise between about 1% to about 99% of the total polymer in the polymer solution blend. In other embodiments, a first, second and third polymer may be used in the polymer blend. In such an embodiment, the third polymer may comprise between about 1% to about 99% of the total polymer in the polymer-solvent blend.

Polyethylene oxide (PEO) is of particular interest as a polymer that is blended with the one or more polymers listed above. PEO is biodegradable and biocompatible, it is hydrophilic and it produces homogenous blend solutions with PLA resulting in a more uniform hybrid electrospun fibers. PEO is typically more hydrophilic and will biodegrade at a faster rate than the other polymers described above. When combined in amounts up to about 50% with one of the other polymers, it will vary fiber surface morphology (e.g., the size and number of surface pores on the fiber), the degradation rate of the matrix structure, and may also affects the release rate of the active. For example, the fiber surface pore distribution may vary with the amount of PEO in the polymer blend. In an embodiment, the more the PEO in the blend, fewer pores are formed on the fiber surface and there is less uniformity in pore sizes. With increased amounts of PEO in the polymer blend, the degradation rate may also increase. In addition, the integrity of the fiber structure and fiber diameter distribution may change as well.

In an embodiment, blends of polymers may be used to form the nanofiber nonwoven fabric. For example, a blend of polylactic acid and polyethylene oxide may be used. The polylactic acid (PLA) may be blended with polyethylene oxide (PEO) at levels of 90% PLA/10% PEO, 80% PLA/20% PEO, 70% PLA/30% PEO, and 50% PLA/50% PEO. Other blends with more PEO are also possible, but preferably the PEO content in these other blends would not exceed about 50%.

Preferably, solvents used in electrospinning are compatible with the plant virus nanoparticles. In an embodiment, the solvents are compatible with RCNMV. Polar solvents, however, are typically suitable for electrospinning due to the dielectric effect and its impact on charge and fiber formation. Exemplary solvents include dicholoromethan (DMC), ethylene acetate (EA), dichloroethylene (DCE), dimethylformamide (DMF), hexafluoroisopropanol (HIFP), dichloromethane (DCM), tetrahydrofuran (THF), ethyl acetate (EA), chloroform, acetone, heptane, isopropylalcohol, octanol and toluene, and water. Exemplary polymer and solvent combinations are shown in Table 1 below, thought combination not set forth below may be used. In addition to solvents, volatile salts are added to adjust the conductivity of the polymer solution.

TABLE 1

| Polymer | Solvent(s) |
| --- | --- |
| Poly(glycolic acid) (GA) | Hexafluoroisopropanol(HIFP) |
| Poly(lactic acid) (PLA) | Hexafluoroisopropanol(HIFP), Dichloromethane(DCM), Tetrahydrofuran (THF), Ethyl acetate(EA), Chloroform, Acetone |
| Poly(caprolactone)(PCL) | Hexafluoisopropanol(HIFP), Dichloromethane(DCM), Chloroform |
| Polyethylenimin-polyethlenglycol | Water Soluble |
| Cyclodextrin | Water Soluble |
| Ethylene Vinyl Acetate | Dichloromethane |

Experimental tests were conducted to assess the impact that various solvents have on the ability of RCNMV to maintain a sufficient cargo load during electrospinning. RCNMV nanoparticles were loaded with 100 ml of rhodamine 590 chloromide. The loaded RCNMV were then combined with various solvents listed in Table 2 below. Rhodamine loaded RCNMV in a buffer solution was used as a control. Fluorescence and absorbance measurements were carried out on each sample to determine leakage. Leakage, is expressed as L=[a−b/a]*100, where a is the initial amount of rhodamine 590, and b is amount of rhodamine 590 chloromide that remained within the RCNMV after one hour. The leakage, L, thus indicates the percentage of rhodamine 590 chloromide that escaped the plant virus nanoparticle. Leakage tests have shown that RCNMV nanoparticles maintain adequate cargo load when exposed to various solvents used in electrospinning. Less capsid leakage was observed for dicholoromethan sample. However, higher leakage values may be overcome a number of ways, for example by adjusting the amount of loaded plant virus in the polymer solution during electrospinning. Further, in other embodiments, it may be useful to use other solvents with the particular polymer not withstanding the leakage indicating when using the particular solvents below.

TABLE 2

| Solvent | % L |
|---|---|
| dicholoromethan | 11.4 |
| ethylene | 14.2 |
| dichloroethylen | 20.2 |
| dimethylformamid | 76.7 |

By altering the electrospinning conditions, the fiber diameter, surface pore size and pore size distribution may be modified. In an embodiment, a hollow fiber with a porous surface is formed. In other embodiments, only a porous interior is formed, for examples when using PLA a polymer. For hollow fiber embodiments, including when PLA is used, the thickness of the inner wall of the nanofiber can be between about 5 nm and about 1000 nm. In an exemplary embodiment, the thickness of the inner wall is about 70 nm. As described above, the fiber diameter may be up to about 50 µm, or higher. In an exemplary embodiment, the fiber diameter may range between about 5 µm to about 20 µm. The diameter is not limited to this range, and it however, may be less than about 5 µm. The surface pores can have elliptical shape with the pore major axis having a length less than about 600 nm (0.6 µm) and the pore minor axis less than about 600 nm (0.6 µm). In an exemplary embodiment, the mean major mean and minor axis is about 400 nm (0.4 µm) and about 200 nm (0.2 µm), respectively. In other embodiments, however, the major axis can be between about 100 nn and 600 nm. In other embodiments, the pore minor axis may range between about 100 nm and 600 nm.

Biodegradation and/or bioabsorption may be influenced by electrospinning process parameters, polymer selection, and conditions of the delivery site. Electrospinning process variables that influence nanofiber fabric properties include, among others, polymer solution viscosity and polymer solution conductivity. Other variables such as voltage, humidity, temperature, collector-needle/electrode-distance, electrode rotational speed, polymer molecular weight, and the dielectric effect of the solvent can be altered according to the choice of polymer used to influence the rate of biodegradation and/or polymer swelling. The moisture content, temperature, and alkalinity of the delivery site can affect the rate of polymer biodegradation. In embodiments where the nanofiber fabric delivers drugs to human skin, the delivery site may be pre-moistened to facilitate biodegradation release of the active from the plant virus nanoparticle.

Nanofiber fabrics were formed with loaded plant virus nanoparticles imbedded within and/or carried on the nanofiber. Other nanofiber fabrics were formed with a loaded PVN composition coated on the nanofiber fabric. The loaded PVN solution was combined with the polymer solution during electrospinning as described above. As the nanofibers are formed, some of the nanoparticles may migrate to the surface of the fibers. When the nanoparticle virus is on the surface of the fibers, contact with the delivery site may initiate a more immediate release of the active. Alternatively, nanoparticles fully embedded within the fiber structure may release the active as the nanofibers biodegrade or swell. Further, coated nanofiber fabrics could display an immediate release of the actives at the delivery site.

Examples A through D below summarize some exemplary embodiments of the present invention. Nanofiber nonwoven fabrics were formed using PLA, and combinations of PEO and PLA, though PEO alone may be formed with water as solvent. Example D summarizes some process parameters and physical characteristics for a PEO/PLA fabric coated with a composition of the loaded PVNs. In either of the exemplary embodiments summarized below, the polymer solution included loaded RCNMV. The polymer solution was electrospun using a Nanospider™ electrospinning machine.

EXAMPLE A

| | |
|---|---|
| Polymer/Polymer Blend | PLA |
| Solvent | DCM |
| Polymer-Solvent Blend | 89% DCM/11% PLA |
| Active | Doxorubicin |
| Volume Ratio of Polymer-Solvent Blend/PVN Solution | 2:1 |
| Flow Rate | 0.9-3.0 mL/min |
| Voltage | 10-12 kV |
| Mean Fiber Size | 7 µm-20 µm |
| Range Pore Size (Major Axis) | 100-600 nm |
| Range Pore Size (Minor Axis) | 100 600 nm |

EXAMPLE B

| | |
|---|---|
| Polymer/Polymer Blend | 70% PLA/30% PEO |
| Solvent | DCM |
| Polymer-Solvent Blend | 88% DCM/12% Pol. Blend |
| Active | Doxorubicin |
| Volume Ratio of Polymer-Solvent Blend/PVN Solution | 2:1 |
| Flow Rate | 0.3-0.7 mL/min |
| Voltage | 10-12 kV |
| Mean Fiber Size | 6.1 µm +/0.7 µm |
| Range Pore Size (Major Axis) | 100-600 nm |
| Range Pore Size (Minor Axis) | 100-600 nm |

EXAMPLE C

| | |
|---|---|
| Polymer/Polymer Blend | 80% PLA/20% PEO |
| Solvent | DCM |
| Polymer-Solvent Blend | 88% DCM/12% Pol. Blend |
| Active | Doxorubicin |
| Volume Ratio of Polymer-Solvent Blend/PVN Solution | 2:1 |
| Flow Rate | 0.3-0.7 mL/min |
| Voltage | 12-13 kV |
| Mean Fiber Size | 6.2 µm ± 1.4 µm |
| Range Pore Size (Major Axis) | 100-600 nm |
| Range Pore Size (Minor Axis) | 100-600 nm |

EXAMPLE D

| | |
|---|---|
| Polymer/Polymer Blend | 90% PLA/10% PEO |
| Solvent | DCM |
| Polymer-Solvent Blend | 88% CDM/12% Pol. Blend |
| Active | Doxorubicin |
| Volume Ratio of Polymer-Solvent Blend/PVN Solution | 2:1 |
| Flow Rate | 0.3-0.7 mL/kV |
| Voltage | 10-12 kV |
| Mean Fiber Size | 7.9 μm ± 1.7 μm |
| Range Pore Size (Major Axis) | 100-600 nm |
| Range Pore Size (Minor Axis) | 100-600 nm |

The nanofiber nonwoven fabric has several applications. In an embodiment, the nanofiber nonwoven fabric may be used for intratumoral chemotherapy, therapeutic agents, implants, or transdermal patches.

An embodiment is a transdermal drug delivery system comprising a non-woven fabric formed of at least one biodegradable and biocompatible polymer and a nanoparticle of a plant virus, wherein the nanoparticle comprises one or more active.

Another embodiment is a method of delivering an active to a delivery site, such as tissue, organ, or bone. The method includes providing a biodegradable and biocompatible electrospun nonwoven fabric formed of at least one biodegradable and biocompatible polymer and a loaded nanoparticle of a plant virus. The method includes applying the biodegradable and biocompatible nonwoven fabric to either of the tissue, organ or bone. The co-spun or the coated embodiments as discussed above may be used on the tissue, organ, bone, or transdermally, such as, using a transdermal patch, for example, by using technology available from Novartis and Alza Corporation.

Another embodiment includes a method for delivering an active to a delivery site, such as a tissue, organ, or bone, using an implant. The method includes providing an implant for insertion on or in a tissue, organ or bone. A biodegradable and biocompatible nonwoven fabric having a loaded nanoparticle of a plant virus is applied to a portion of the implant. The co-spun or the coated embodiments as discussed above may be used on the implant.

In another embodiment, the nanofiber nonwoven fabric may be used as a tissue engineering scaffold. For example a biodegradable and biocompatible nanofiber nonwoven fabric having a loaded nanoparticle of a plant virus may be used as a tissue scaffold. The co-spun or the coated embodiments as discussed above may be used on the implant.

Although the present invention has been described with exemplary embodiments, it is to be understood that modifications and variations may be utilized without departing from the spirit and scope of the invention, as those skilled in the art will readily understand. Such modifications and variations are considered to be within the purview and scope of the appended claims and their equivalents.

What is claimed is:

1. A biodegradable active delivery system comprising: an electrospun nonwoven fabric, the fabric comprising
   a. fibers formed from at least one biodegradable and biocompatible polymer; and
   b. nanoparticles embedded in the fibers, the nanoparticles comprising at least one active infused into a purified capsid of a plant virus.

2. The biodegradable active delivery system according to claim 1, wherein said biodegradable polymer is selected from the group consisting of polyglycolic acid, polylactic acid, polyethylene oxide, polycaprolactone, polyethylenimine-polyethylene glycol, cyclodextrin, and ethylene vinyl acetate, poly(L-lysine)-poly(ethylene glycol), polyethylenimine, poly(a[4-aminobutyl]-1-glycolic acid), cyclodextrin, Poly(2-(dimethylamino)ethyl methacrylate), poly(vinyl alcohol), poly(enol-ketone), and N-(2-hydroxypropyl) methacrylamide copolymers.

3. The biodegradable active delivery system according to claim 1, wherein the fibers are formed from at least a first polymer and a second polymer, both the first and second polymers selected from the group consisting of polyglycolic acid, polylactic acid, polyethylene oxide, polycaprolactone, polyethylenimine-polyethylene glycol, cyclodextrin, and ethylene vinyl acetate, poly(L-lysine)-poly(ethylene glycol), polyethylenimine, poly(a[4-aminobutyl]-1-glycolic acid), cyclodextrin, Poly(2-(dimethylamino)ethyl methacrylate), poly(vinyl alcohol), poly(enol-ketone), and N-(2-hydroxypropyl) methacrylamide copolymers.

4. The biodegradable active delivery system according to claim 1, wherein the fibers are formed from a first biodegradable polymer selected from the group of polymers consisting of polyglycolic acid, polylactic acid, polycaprolactone, polyethylenimine-polyethylene glycol, cyclodextrin, and ethylene vinyl acetate, poly(L-lysine)-poly(ethylene glycol), polyethylenimine, poly(a-[4-aminobutyl]-1-glycolic acid), cyclodextrin, Poly(2-(dimethylamino)ethyl methacrylate), poly(vinyl alcohol), poly(enol-ketone), and N-(2-hydroxypropyl) methacrylamide copolymers, and a second polymer which is polyethylene oxide.

5. The biodegradable active delivery system according to claim 1, wherein the purified capsid is from a plant virus selected from the group of virus families consisting of the Tombusviridae family, the Comaviridae family and the Bromoviridae family.

6. The biodegradable active delivery system according to claim 1, wherein the purified capsid is from a plant virus that is rendered harmless to the subject and can be imbedded in or on the nanofibers.

7. The biodegradable active delivery system according to claim 1, wherein the purified capsid is from a plant virus selected from the group consisting of red clover necrotic mosaic virus, artichoke mottled crinkle virus, carnation italian ringspot virus, cucumber necrosis virus, cymbidium ringspot virus, eggplant mottled crinkle virus, grapevine algerian latent virus, lato river virus, moroccan pepper virus, neckar river virus, pelargonium leaf curl virus, petunia asteroid mosaic virus, sitke waterborne virus, and the tomato bushy stunt virus.

8. The biodegradable active delivery system according to claim 1, wherein the purified capsid is from the red clover necrotic mosaic virus.

* * * * *